(12) United States Patent
Moss

(10) Patent No.: US 9,770,292 B2
(45) Date of Patent: Sep. 26, 2017

(54) MEDICAL DEVICE FOR EVALUATING A TEMPERATURE SIGNAL

(71) Applicant: BIOTRONIK AG, Buelach (CH)

(72) Inventor: Christian Moss, Berlin (DE)

(73) Assignee: BIOTRONIK AG, Buelach (CH)

( * ) Notice: Subject to any disclaimer, the term of this patent is extended or adjusted under 35 U.S.C. 154(b) by 446 days.

(21) Appl. No.: 14/483,102

(22) Filed: Sep. 10, 2014

(65) Prior Publication Data

US 2015/0088119 A1 Mar. 26, 2015

Related U.S. Application Data

(60) Provisional application No. 61/882,649, filed on Sep. 26, 2013.

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 18/1233* (2013.01);
(Continued)

(58) Field of Classification Search
CPC . A61B 18/1492; A61B 18/12; A61B 18/1206; A61B 2018/1253; A61B 2018/126; A61B 18/14; A61B 18/1233; A61B 2090/065; A61B 2018/00577; A61B 2018/00636; A61B 2018/00642; A61B 18/00648; A61B 2018/00666; A61B 2018/00672; A61B 2018/00678; A61B 2018/00696; A61B 2018/00702;
(Continued)

(56) References Cited

U.S. PATENT DOCUMENTS 6,063,078 A * 5/2000 Wittkampf ......... A61B 18/1492
606/41
2002/0123749 A1 9/2002 Jain
(Continued)

FOREIGN PATENT DOCUMENTS

EP 0566725 6/2003
EP 2338430 8/2012
(Continued)

OTHER PUBLICATIONS

European Search Report received from EP Application Serial No. 14180599, dated Mar. 11, 2015, 7 pages.

*Primary Examiner* — Ronald Hupczey, Jr.
*Assistant Examiner* — Jennifer Le
(74) *Attorney, Agent, or Firm* — Arc IP Law, PC; Joseph J. Mayo

(57) ABSTRACT

A medical device including an evaluation unit and an electrode line. The electrode line includes at least one temperature sensor. The temperature sensor delivers a temperature signal to the evaluation unit. The evaluation unit evaluates periodic fluctuations of a signal level of the temperature signal and generates an evaluation output signal qualifying constant wall touching of the electrode line according to whether periodic fluctuations of a signal level of the temperature signal lie below or above a predetermined limit value.

16 Claims, 13 Drawing Sheets

(51) Int. Cl.
*A61B 18/00* (2006.01)
*A61B 90/00* (2016.01)
(52) U.S. Cl.
CPC .............. *A61B 18/12* (2013.01); *A61B 18/14* (2013.01); *A61B 2018/00577* (2013.01); *A61B 2018/00636* (2013.01); *A61B 2018/00642* (2013.01); *A61B 2018/00648* (2013.01); *A61B 2018/00666* (2013.01); *A61B 2018/00672* (2013.01); *A61B 2018/00678* (2013.01); *A61B 2018/00696* (2013.01); *A61B 2018/00702* (2013.01); *A61B 2018/00708* (2013.01); *A61B 2018/00714* (2013.01); *A61B 2018/00732* (2013.01); *A61B 2018/00773* (2013.01); *A61B 2018/00791* (2013.01); *A61B 2018/00845* (2013.01); *A61B 2018/00875* (2013.01); *A61B 2018/126* (2013.01); *A61B 2018/1253* (2013.01); *A61B 2090/065* (2016.02)
(58) Field of Classification Search
CPC   A61B 2018/00708; A61B 2018/00773; A61B 2018/00791; A61B 2018/00845; A61B 2018/00875; A61B 2018/00863; A61B 2018/00839; A61B 2018/00904
USPC ......................................................... 606/34
See application file for complete search history.

(56) References Cited

U.S. PATENT DOCUMENTS

2003/0204184 A1* 10/2003 Ferek-Patric ...... A61B 18/1492
606/41
2007/0191829 A1*  8/2007 McGee ................. A61B 18/14
606/41
2012/0136346 A1*  5/2012 Condie ............. A61B 18/1206
606/33

FOREIGN PATENT DOCUMENTS

EP          1827277       12/2012
WO      2008035070 A2     3/2008

* cited by examiner

MEDICAL DEVICE FOR EVALUATING A TEMPERATURE SIGNAL

This application claims the benefit of U.S. Provisional Patent Application 61/882,649 filed on 26 Sep. 2013, the specification of which is hereby incorporated herein by reference.

BACKGROUND OF THE INVENTION

Field of the Invention

Embodiments of the invention generally relate to a medical device that evaluates a temperature signal.

Description of the Related Art

Catheters are often used nowadays in medical applications in order to reach regions or cavities of a patient that are located within the body. Catheters are generally flexible tubes, which may carry out various functions depending on their design. For example, a catheter may be equipped with electrodes in order to transmit energy to tissue arranged around the electrodes. Catheters having electrodes are typically used for example for renal denervation, in which afferent sympathetic nerve fibers (of the sympathetic nervous system) in the renal arteries are selectively severed or cauterized by the transfer of thermal energy to the nerve fibers. Renal denervation is generally used for the therapy of therapy-resistant arterial hypertension, which is defined as high blood pressure, which, in spite of drug-based therapy with antihypertensive drugs, including at least one diuretic, is typically not in the desired target blood pressure range.

The process of checking the exact amount of energy that is transferred from the electrodes to the tissue is generally impeded by the fact that the position of the catheter at the site of use cannot be accurately checked. As a result, the catheter, in certain circumstances, is not in direct contact with the tissue to which the energy is to be transferred, and some of the energy is instead transferred to the blood. This may typically lead to coagulation or clumping of the blood, which has to be absolutely avoided in view of safe therapy. In this case, the clumped blood may cause damage to the organs due to the closure of blood vessels, and in the worst case scenario may also close brain or heart vessels, which may lead to the death of the patient. Wall contact between electrodes and tissue is therefore essential for successful execution of the renal denervation procedure. A strategy for avoiding damage is to increase the energy transfer in steps in order to generate a slower temperature rise, which generally poses a lower risk of causing the blood to clump.

To determine the wall contact, the temperature rise over time or the impedance of the tissue is generally measured, since the impedance typically decreases with longer duration of the energy transfer to the tissue. Animal tests have shown however that, by evaluating the impedance alone, it may not be possible to come to a conclusion regarding the presence of reliable wall contact. The lack of wall contact may be measured for example by a low or absent temperature rise after energy transfer. The evaluation of the temperature rise is generally time-consuming however, which is a disadvantage with use as a switch-off criterion.

European Patent 0566725 entitled "Ablation Electrode With Insulated Temperature Sensing Elements", to Stuart et al., presents an ablation electrode for ablation catheters having thermally insulated thermal sensors. The ablation catheter of Stuart et al. has an energy-emitting body, connected to an energy source, for contacting tissue, the body containing temperature sensors which are arranged on the body and are thermally insulated therefrom. The temperature sensors of Stuart et al. measure the temperature of the tissue and are connected to a high-frequency generator, which generates the energy for the energy-emitting body. According to Stuart et al., the energy transfer of the high-frequency generator may be adapted in accordance with the measured temperature at the temperature sensors or a measured impedance of the tissue in order to obtain a temperature of the tissue in specific temperature ranges or impedance ranges.

For example, European Patent 2338430 entitled "Catheter With Strain Gauge Sensor", to Govari, discloses a medical probe having strain gauge sensors. The probe of Govari includes a flexible insertion tube, of which the distal end is designed to be brought into contact with tissue of a body cavity, and a sensor tube, which contains an elastic material in the distal end of the flexible insertion tube, the material being designed to deform in response to forces acting from the tissue onto the distal end. According to Govari, a multiplicity of strain gauge sensors are applied at various points to the surface of the sensor tube and generate a respective signal in response to deformations of the sensor tube. The probe further includes at least one temperature-compensating strain gauge sensor, which is designed to generate signals in order to compensate for changes in temperature in the multiplicity of strain gauge sensors.

European Patent 1827277 entitled "Catheter With Multiple Microfabricated Temperature Sensors", to Nakagawa et al., presents a catheter having a plurality of microfabricated temperature sensors. The temperature sensors of Nakagawa et al. are arranged in a vicinity of a tip of a distal end of the catheter on an outer surface. The tip is formed by an electrode. According to Nakagawa et al., the temperature sensors contain a thin sensor layer, of which the resistance may change due to a temperature change. Furthermore, a temperature sensor may surround the periphery of the catheter.

BRIEF SUMMARY OF THE INVENTION

One or more embodiments of the invention relate to a medical device that evaluates a temperature signal, including an evaluation unit and an electrode line with a temperature sensor, and to a method for evaluating a temperature signal using the medical device.

At least one embodiment of the invention includes a medical device and a method to detect constant wall touching of an electrode line or contact between a wall and an electrode line.

One or more embodiments of the invention include a medical device having an evaluation unit and an electrode line, which includes at least one temperature sensor. In at least one embodiment, the temperature sensor may deliver a temperature signal to the evaluation unit. In one or more embodiments, the evaluation unit may evaluate periodic fluctuations of a signal level of the temperature signal and may generate an evaluation output signal, qualifying constant wall touching of the electrode line, depending on whether periodic fluctuations of a signal level of the temperature signal lie below or above a predetermined limit value.

The inventors have recognized that periodic fluctuations of a signal level of a temperature signal, in one or more embodiments, provide a quick criterion to determine constant wall touching. As such, in at least one embodiment, it possible to save energy, since an unnecessary energy transfer, should the electrode line not be in contact with the wall, to a fluid surrounding a wall may be reduced. In at least one embodiment, the criterion may be used to decide more quickly when the energy transfer is to be interrupted. In one or more embodiments, the electrode line may then be realigned in order to produce wall contact. In at least one embodiment, the criterion may also be used for example to interrupt the energy transfer in the case of poor wall contact in a renal denervation procedure. In one or more embodiments, good wall contact may be identified faster, for example between a bipolar electrode line or a bipolar catheter and the wall, if there is no frequency component of the heart rate in the spectrum of temperature. The energy transfer, in at least one embodiment, may be interrupted more quickly should the spectrum have a frequency component of the heart rate. According to one or more embodiments, the quicker interruption of the energy transfer in the event of poor wall contact reduces blood clotting and the formation, triggered thereby, of blood clots, which may lead to blockages in the blood vessels and damage in the body of the patient.

In at least one embodiment of the invention, the electrode line may be flexible, whereby it may be pushed into internal curved cavities, for example into vessels or organs of a body, artificial organs of a test system or of an active ingredient recovery system, or into other vessels or fluid lines. In one or more embodiments, the electrode line may be a catheter. In at least one embodiment, the catheter may have a coating or may be an uncoated catheter. In at least one embodiment, the electrode line may include a flexible tube. In one or more embodiments, the electrode may be cooled, for example a coolant may be guided inside the flexible tube of the electrode line. In at least one embodiment, the electrode line may be an ablation catheter with an ablation electrode. In one or more embodiments, the catheter may be a special catheter for renal denervation. In at least one embodiment, the electrode line may also include an expandable balloon, for example at its distal end, or may be a balloon catheter.

By way of at least one embodiment, the one or more temperature sensors may be arranged in the vicinity of the electrode or electrodes. In one or more embodiments, the temperature sensor or the temperature sensors may be arranged in the vicinity of an ablation electrode. In at least one embodiment, a plurality of temperature sensors may also be arranged in the vicinity of a respective ablation electrode. In one or more embodiments, the electrode line may include a temperature sensor running around the periphery of the electrode line. In at least one embodiment, the temperature sensors may be thermally insulated from the electrodes. In one or more embodiments, the temperature sensors may be arranged on an outer surface of the electrode line. For example, in at least one embodiment, the temperature sensors may be thermocouples, sensor layers of which the electrical resistance changes with a change in temperature, or the like.

In at least one embodiment of the invention, the electrode line of the medical device may include a bipolar electrode line, for example a bipolar catheter or the like, having an ablation electrode pair for a bipolar ablation. According to one or more embodiments, the two ablation electrodes may be arranged here at a short distance from one another, which is suitable to carry out an ablation process with the aid of both ablation electrodes since the electrodes close an electric circuit via a wall. In the case of a bipolar electrode line, in at least one embodiment of the invention, the evaluation unit may generate an evaluation output signal indicating constant wall touching of the bipolar electrode line if periodic fluctuations of a signal level of the temperature signal lie below the predetermined limit value. Additionally or alternatively, in one or more embodiments, the evaluation unit may also generate an evaluation output signal indicating no constant wall touching of the bipolar electrode line if periodic fluctuations of a signal level of the temperature level lie above the predetermined limit value. By way of at least one embodiment, example measurements have shown that the failure to reach a target temperature of 70° C. may lead to a maximum value from 0.6° C. to 1.0° C. for periodic fluctuations of a signal level of the temperature signal in the temperature spectrum if there is no constant wall touching of the bipolar electrode line, and may lead to a maximum value of 0.08° C. if there is constant wall touching of the bipolar electrode line. In one or more embodiments, a predetermined limit value may be established therefrom. In at least one embodiment, the predetermined limit value may include a value between 0.1° C. and 1.0° C., such as a value between 0.2° C. and 0.8° C., or a value between 0.3° C. and 0.6° C.

In at least one embodiment of the invention, the electrode line of the medical device may include a unipolar electrode line, for example a unipolar catheter with counter electrode or neutral electrode or the like, with an ablation electrode for unipolar ablation. In one or more embodiments, one ablation electrode may be in electrical contact with a neutral electrode secured outside the system containing a wall, for example secured to a body, the neutral electrode being able to carry out an ablation process with the aid of the ablation electrode since it closes an electric circuit through a wall and for example the body with the ablation electrode. In the case of a unipolar electrode line, according to at least one embodiment, the evaluation unit may generate an evaluation output signal indicating constant wall touching of the unipolar electrode line if periodic fluctuations of a signal level of the temperature signal lie above the predetermined limit value. Additionally or alternatively, in at least one embodiment, the evaluation unit may also generate an evaluation output signal indicating no constant wall touching of the unipolar electrode line if periodic fluctuations of a signal level of the temperature signal lie below the predetermined limit value. In one or more embodiments, example measurements have shown that the failure to reach a target temperature of 70° C. may lead to a maximum value of 0.1° C. of periodic fluctuations of a signal level of a temperature signal in the temperature spectrum if there is no constant wall touching of the electrode line, whereas constant wall touching may be found for maximum values above 0.2° C. In at least one embodiment, a predetermined limit value may be established therefrom. The predetermined limit value, in one or more embodiments, may include a value between 0.05° C. and 0.6° C., such as a value between 0.1° C. and 0.4° C., or a value between 0.2° C. and 0.3° C.

In at least one embodiment, the medical device may include an energy source. In one or more embodiments, the energy source may be electrically connected to the electrode line and may feed energy to the electrode line. In at least one embodiment, the energy source may also be electrically connected to the evaluation unit. In this case, according to one or more embodiments, the evaluation unit may generate an energy source switch-off signal if the evaluation unit generates or has generated an evaluation output signal indicating no constant wall touching of the electrode line. In at least one embodiment, the evaluation unit, in order to switch off the energy source, may transmit the energy source switch-off signal to the energy source or a control unit of the energy source. During operation of the energy source, in one or more embodiments, the energy source switch-off signal may switch off or interrupt the energy transfer from the energy source to the electrode line, for example for an ablation process.

In at least one embodiment, an electrode line may be used for renal denervation, for example in a renal artery of a kidney or in an artificial renal artery of an artificial test system. By way of one or more embodiments, in the case of renal denervation with a bipolar electrode line, for example a bipolar catheter, the energy source may be switched off with insufficient wall contact based on the detection of a pulse rate in the temperature signal during the energy transfer. Once the energy transfer has started, in at least one embodiment, a time/frequency transform of the temperature data may be calculated continuously. In one or more embodiments of the invention, the temperature data may be obtained from the analog temperature signal of the temperature sensor by firstly amplifying this signal in a temperature signal amplifier, for example with integrated cold junction compensation, and then digitalizing the signal in an analog-to-digital converter. If necessary, in at least one embodiment, the digitalized temperature signal may also be encoded in a microcontroller unit and may be provided to a computer unit for evaluation. Alternatively, in one or more embodiments, the digitalized temperature signal may also be evaluated in an ablation generator or the evaluation unit. In the case of an energy transfer in the event of renal denervation, according to at least one embodiment of the invention, the tissue of the renal artery located around the electrodes may heat up when there is wall contact or constant wall touching. As such, the heating process may be used to cauterize sympathetic nerve fibers, and the blood flow through the renal artery has only a small influence on the heat development or the temperature curve. As such, in one or more embodiments, pulse rate is therefore not visible in the spectrum with a time/frequency transform of the temperature data. If the catheter has poor wall contact or no constant wall touching, according to at least one embodiment, the temperature curve may be influenced by the blood flow (volume flow rate)

$$F = \frac{dV}{dt},$$

where V is the blood volume and t is time. As a result of the activity of the heart, in one or more embodiments, the blood flow may be subject to a constant change in the heart rhythm. In at least one embodiment, with poor wall contact, this may lead to a cooling effect, which is visible as pulse rate in the temperature spectrum.

By way of one or more embodiments, renal denervation may also be carried out with a unipolar electrode line. In at least one embodiment, with use of a unipolar electrode line, for example of a unipolar catheter, the effect reverses. In one or more embodiments, energy is supplied via a high-frequency supply from the energy source to the electrode line for energy transfer. In at least one embodiment, a neutral electrode (such as an adhesive electrode) may be secured to the body outside the body. In contrast to the bipolar catheter, in one or more embodiments, the pulse rate is not visible in the temperature spectrum in the event of poor wall contact. According to one or more embodiments, with good wall contact however, a weak amplitude of the pulse rate presents itself in the temperature spectrum of the unipolar catheter.

One or more embodiments of the invention use the measuring principle for the identification of constant wall touching in the case of renal denervation even before therapy is begun in order to determine the quality of the wall contact. For example, in at least one embodiment, with a bipolar catheter, a low power that may lead only to an insignificant heating of the environment surrounding the catheter may be delivered for a short period of time. As such, in at least one embodiment, the quality of the wall contact may be concluded on the basis of an evaluation of the temperature data.

In one or more embodiments, the evaluation of the periodic fluctuations of a signal level of the temperature signal may be enabled with the aid of a time/frequency transform of the temperature signal. The time/frequency transform, in at least one embodiment, may be a Fourier transform for example, which is carried out with use for example of an FFT (fast Fourier transform), wavelet transform, short-time Fourier transform algorithm, or the like.

In one or more embodiments, the frequency range of the time/frequency-transformed temperature signal may be evaluated for example between 0 Hz (0 bpm (beats per minute)) and 20 Hz (1200 bpm), such as between 0.2 Hz (12 bpm) and 4.2 Hz (252 bpm), between 0.8 Hz (48 bpm) and 3.4 Hz (204 bpm), or between 1.1 Hz (66 bpm) and 2.0 Hz (120 bpm).

In at least one embodiment, the method for evaluating a temperature signal with use of the medical device includes the step of providing a temperature signal and a step of evaluating the periodic fluctuations of a signal level of the temperature signal. The temperature signal, in one or more embodiments, may not be supplied from a temperature sensor and for example may also be generated artificially. In one or more embodiments, the method may include generating an evaluation output signal qualifying constant wall touching of the electrode line according to whether periodic fluctuations of a signal level of the temperature signal lie below or above a predetermined limit value. On average, according to one or more embodiments, at least 3.3 measured temperature values per second may be evaluated for example, such as at least 6.6 measured temperature values per second, or at least 22 measured temperature values per second.

In at least one embodiment, the method may include a step in which a time/frequency transform of the temperature signal is carried out. For this purpose, in one or more embodiments, an analog signal may first be digitalized for example, and the digitalized signal may then be transformed via a time/frequency transform from the time domain into the frequency range. On average, in at least one embodiment, at least 3.3 measured temperature values may be used per second for example (corresponding to a sampling rate (sampling frequency) of 3.3 Hz), such as at least 6.6 measured temperature values per second (corresponding to a sampling rate of 6.6 Hz), or at least 22 measured temperature values per second (corresponding to a sampling rate of 22 Hz), in order to carry out the time/frequency transform of the temperature signal. In one or more embodiments, the time/frequency-transformed signal may then be evaluated for example via the evaluation of the amplitudes of preferred frequency ranges.

By way of at least one embodiment, the sampling frequency $f_s$ that digitalized the temperature data may be twice as large as the maximum frequency occurring in the analog temperature signal. In at least one embodiment, the maximum frequency may be predefined by a pulse rate of a human, therefore temperature signals up to 3.333 Hz (200 bpm) may be captured. In one or more embodiments, the sampling frequency may be at least 6.667 Hz. In order to avoid aliasing effects, according to at least one embodiment, $f_s$ with a frequency of at least 10 Hz may be used, such as with a frequency of 22 Hz, or with a frequency of at least 100 Hz. In one or more embodiments, the digitalized data may be transformed using an algorithm for time/frequency transform, for example FFT (fast Fourier transform) into the frequency range. In at least one embodiment, the smaller the frequency resolution may be, the greater may be the number N of points selected that are included in the calculation. In one or more embodiments, the number N of points may be given by $$N = \frac{f_s}{\Delta f},$$

wherein $\Delta f$ specifies the resolution in the frequency range. For example, in at least one embodiment, for a resolution of the pulse rate of 0.167 Hz (10 bpm), $$N = \frac{22 \text{ Hz}}{10/60 \text{ s}} = 132$$

are therefore required. In one or more embodiments, the algorithm to calculate the FFT may only operate at data lengths which correspond to a power of two, therefore a data length or number N of 128 or 256, which for example may be generated by shortening the data length or supplementing with zeros, is therefore required. In at least one embodiment, the time T for the capture of N data values may be $$T = N \cdot \frac{1}{f_s}.$$

With a sampling rate of 22 Hz, in one or more embodiments, a recording over 6 s may be necessary for a pulse rate resolution of 0.67 Hz (10 bpm). According to at least one embodiment, the method allows for quick detection of the pulse rate in the data, whereby it is ensured that the energy transfer is switched off reliably. One or more embodiments of the invention may determine within 3 s after onset of the energy transfer whether a component of the pulse rate is present in the data.

In at least one embodiment of the method, the method, as a first step, may include a starting of an energy transfer, for example of the energy source to the electrode line. In one or more embodiments, the method may include a step that includes a termination of the energy transfer, for example from the energy source to the electrode line, if the evaluation unit generates or has generated an evaluation output signal indicating no constant wall touching of the electrode line.

In at least one embodiment of the invention, the medical device may include a pulse generator unit that generates a pulsed fluid flow. In one or more embodiments, the pulse generator unit for example may supply the cavity of an artificial organ or the like with a fluid and may generate a pulse rate for the fluid flow. According to at least one embodiment, the pulse generator unit may also generate a varying pulse, for example with the aid of a randomized procedure in a predetermined frequency range.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
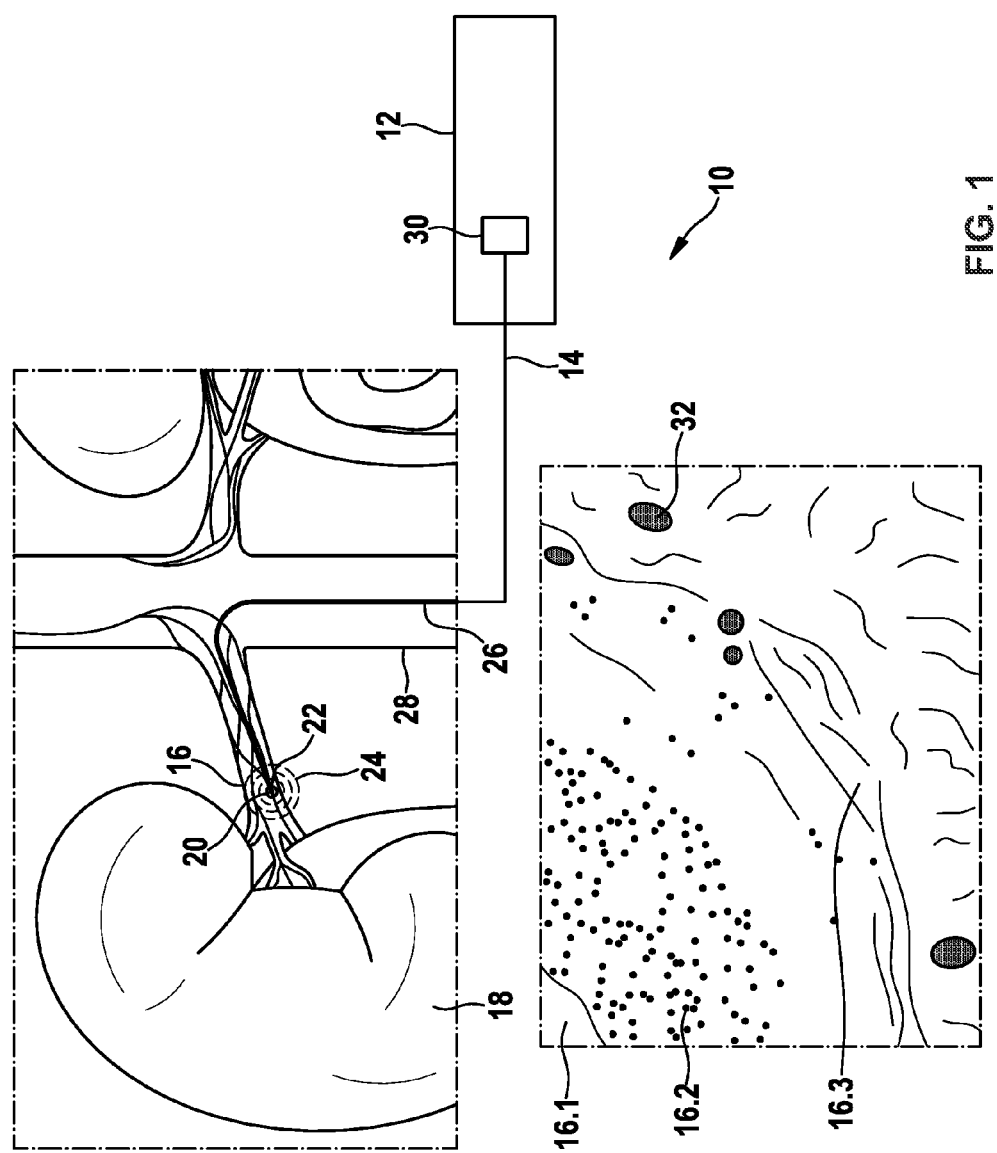
FIG. 1 shows a first exemplary embodiment of a medical device having an electrode line in a renal artery of a kidney.

FIG. 1 shows a first exemplary embodiment of a medical device 10 having an evaluation unit 12 and an electrode line 14, which is introduced into a renal artery 16 of a kidney 18 according to one or more embodiments of the invention. The lower part of FIG. 1 shows a part of a cross section of a renal artery vessel 16 with the vessel volume 16.1, media 16.2 and adventitia 16.3. One or more embodiments of the invention may include a temperature sensor 20 that delivers a temperature signal of the environment surrounding an ablation electrode 22, which may change due to an energy transfer 24 of the ablation electrode 22. At least one embodiment of the invention may include an electrode line 14 surrounded by a flexible tube 26 that extends along the renal artery 16 and the aorta 28 to the evaluation unit 12, and may transmit the temperature signal from the temperature sensor 20 to the evaluation unit 12. The evaluation unit 12, in one or more embodiments, may evaluate periodic fluctuations of a signal level of the temperature signal of the temperature sensor 20 and may generate an evaluation output signal qualifying constant wall touching depending on whether periodic fluctuations of a signal level of the temperature signal lie below or above a predetermined limit value. The evaluation unit 12 of the medical device 10, in at least one embodiment, may include an energy source 30. In one or more embodiments the energy source 30 supplies the electrode line 14 with energy, which may be used for energy transfer 24 to sympathetic nerve fibers 32 and therefore for cauterization thereof. In at least one embodiment, the medical device 10 may be used to carry out a renal denervation procedure.

Figure 2:
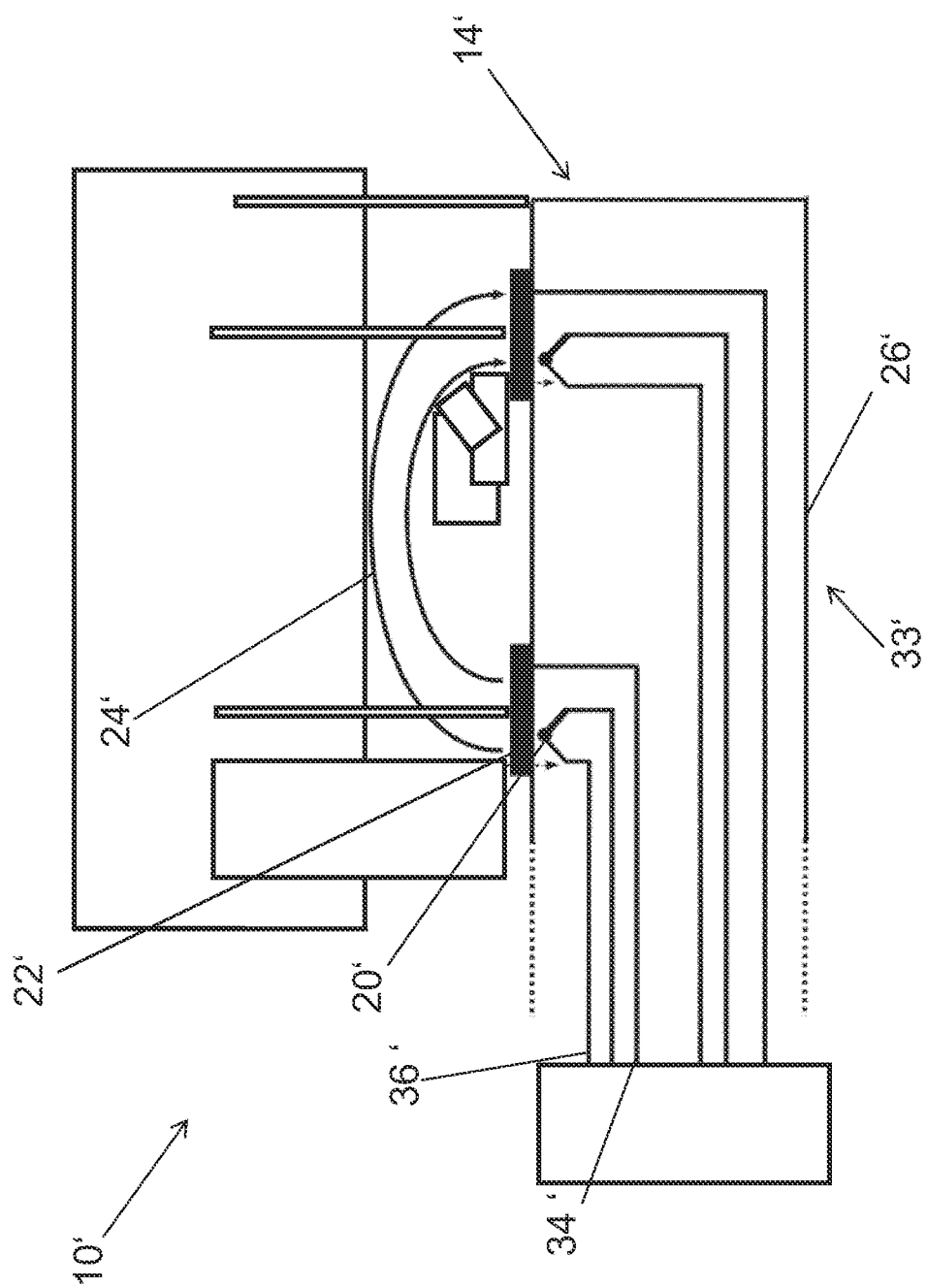
FIG. 2 shows a schematic illustration of an exemplary embodiment of a medical device having a bipolar electrode line.

FIG. 2, as a first exemplary embodiment of the medical device 10', shows a bipolar electrode line 14' according to one or more embodiments of the invention. In at least one embodiment, the bipolar electrode line 14' may include an ablation electrode pair 22' at its distal end 33', and a temperature sensor 20' assigned to the ablation electrodes 22' may be located in the vicinity of each of the ablation electrodes. In one or more embodiments, the ablation electrodes 22' may be supplied with energy from the energy source 30 via the electrical lines 34' and may transfer the energy in the form of an energy transfer 24'. In at least one embodiment, the temperature sensors 20' may be connected via sensor lines 36' to the evaluation unit 12 and may supply temperature signals thereto. In one or more embodiments, a flexible tube 26' may surround the electrical lines 34' and the sensor lines 36', and may insulate the electrical lines 34' and the sensor lines 36' electrically from one another. In at least one embodiment, the flexible tube 26' may also have an inner channel, which may guide a coolant, for example for cooling the ablation electrodes 22' (not shown). In one or more embodiments, the surface of the electrode line 14' may have a coating, for example containing medically effective substances (not shown). In at least one embodiment, the distal end 33' of the electrode line 14' may also be an expandable balloon or an expandable balloon electrode (not shown). In one or more embodiments, electrode lines in the form of special catheters for renal denervation may be provided (not shown). According to at least one embodiment, the temperature sensors 20' may be formed for example as thermocouplers, sensor layers, or the like (not shown). In one or more embodiments, the position of the temperature sensors 20' may also be independent of the position of the ablation electrodes 22'. By way of at least one embodiment, the position of the temperature sensors 20' may be arranged such that a heating induced by energy transfer from the ablation electrodes 22' is captured as completely as possible by the temperature sensors 20'. For example, in one or more embodiments, electrode lines may also have a temperature sensor or a plurality of temperature sensors running around the periphery (not shown).

Figure 3:
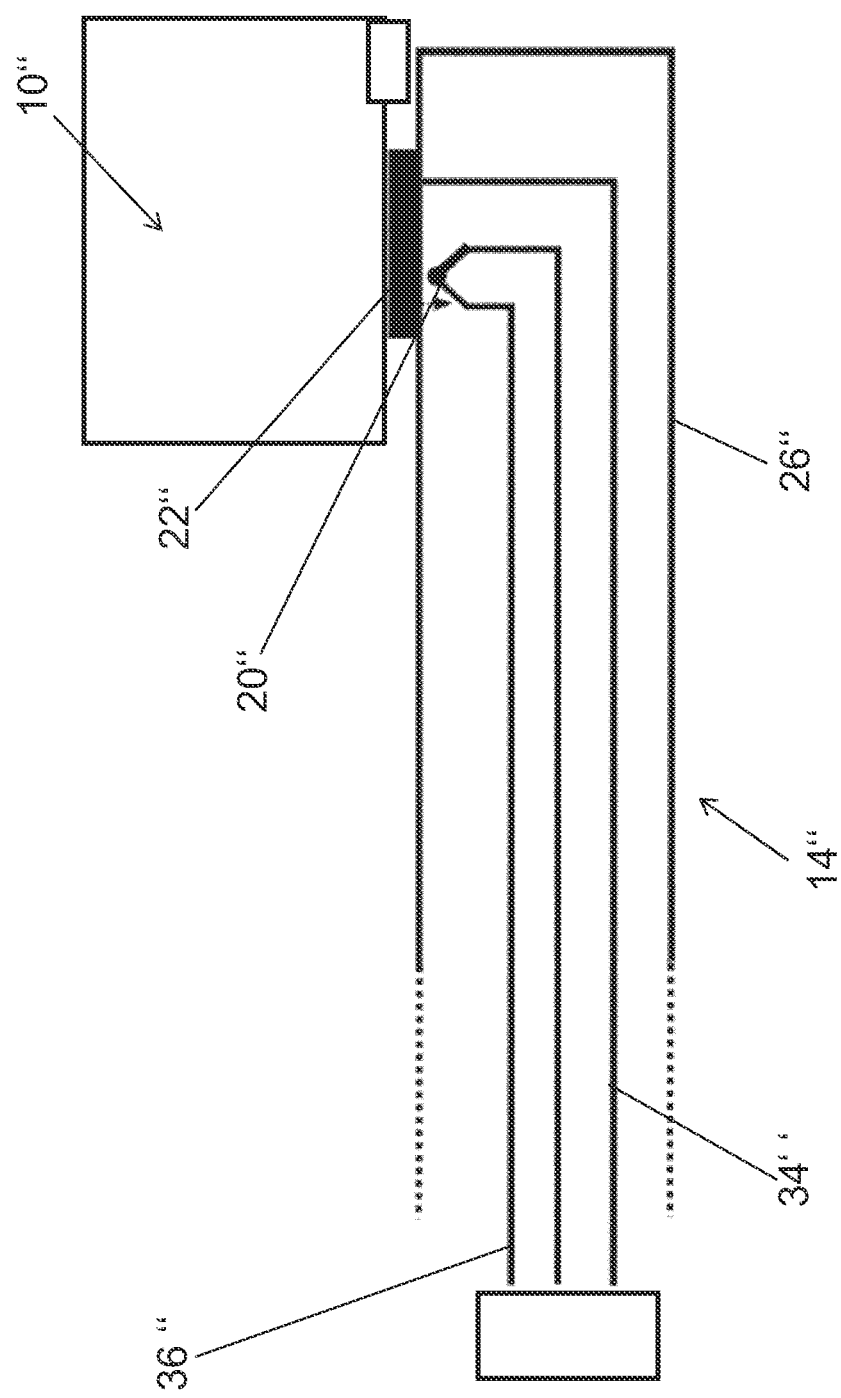
FIG. 3 shows a schematic illustration of an exemplary embodiment of a medical device having a unipolar electrode line.

As a second exemplary embodiment of the medical device 10", FIG. 3 shows a unipolar electrode 14" according to one or more embodiments of the invention. According to at least one embodiment, one ablation electrode 22" may be operated with the aid of a counter electrode arranged at a distance in order to close the electric circuit (not shown). In one or more embodiments, the ablation electrode 22" may be supplied with energy from the energy source 30 via the electrical line 34". In at least one embodiment, the temperature sensor 20" may be arranged in the vicinity of the ablation electrode 22" and may be connected via the sensor lines 36" to the evaluation unit 12, to which the temperature sensor 20" supplies a temperature signal. In one or more embodiments, the flexible tube 26" may surround the electrical lines 34" and the sensor lines 20" and may insulate the lines electrically from one another.

Figure 4:
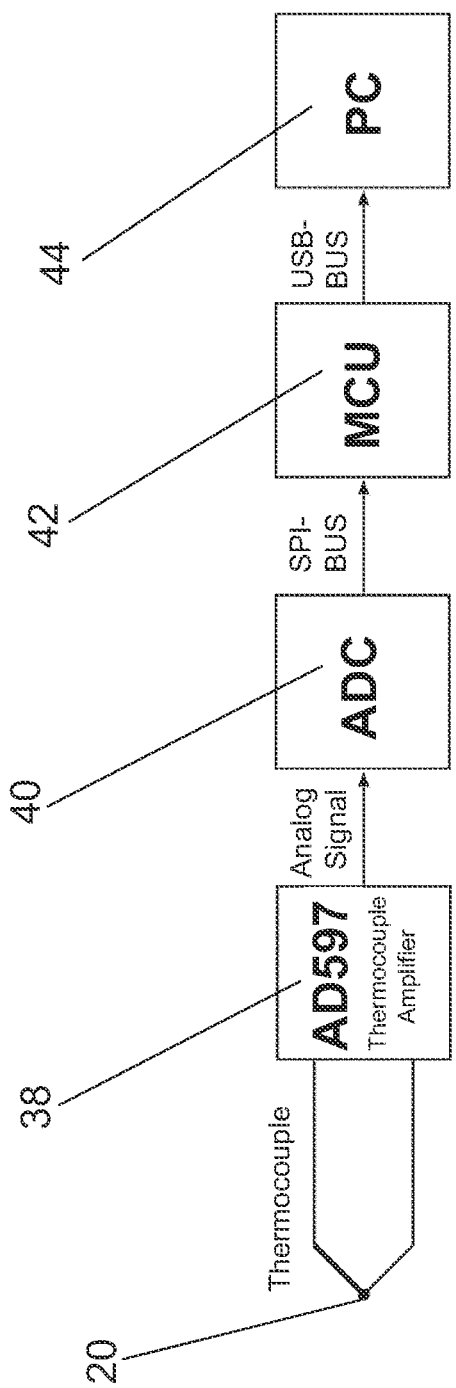
FIG. 4 shows a schematic illustration of an exemplary embodiment of a circuit for evaluating a temperature sensor.

FIG. 4 shows an exemplary circuit for evaluating a temperature signal of a temperature sensor 20 according to one or more embodiments of the invention. In at least one embodiment, the temperature sensor 20 may deliver a temperature signal to a temperature signal amplifier 38, which amplifies the temperature signal with integrated cold junction compensation. In at least one embodiment, the temperature signal amplifier 38 may include an AD597. In one or more embodiments, the temperature signal amplifier 38 may deliver the analog temperature signal to an analog-to-digital converter 40. The analog-to-digital converter 40, in at least one embodiment, converts the analog temperature signal into a digital temperature signal and delivers it to a microcontroller unit 42. In one or more embodiments, the microcontroller unit 42 may encode the digital temperature signal in a computer-readable form and may deliver it to a computer unit 44. In at least one embodiment, the digital temperature signal may be evaluated in the computer unit 44. In at least one embodiment, an ablation generator (not shown) may also be integrated in the circuit instead of the microcontroller unit 42 and the computer unit 44.

Figure 5:
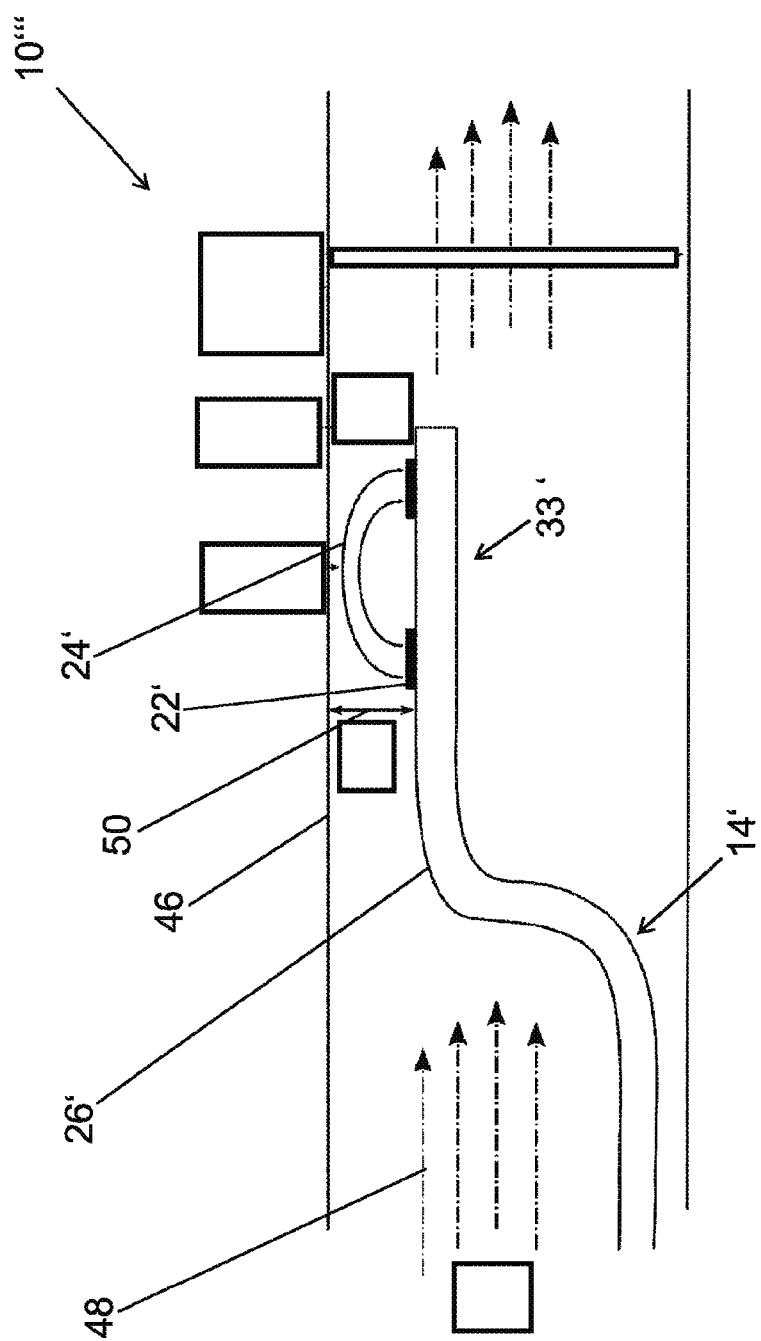
FIG. 5 shows a schematic illustration of an exemplary embodiment of a medical device having a bipolar electrode line in a test system with fluid flow.

According to at least one embodiment, FIG. 5 shows a medical device 10''' in the form of a bipolar electrode line 14' which may be arranged in a tubular cavity having a wall 46. In at least one embodiment, the tubular cavity may include a fluid flow 48, which is directed coaxially with the axis of the electrode line 14'. The distal end 33' of the electrode line 14', in one or more embodiments, may be located in the vicinity of the wall 46. In at least one embodiment, the ablation electrodes 22' may include a wall distance 50, which reduces the energy transfer 24' to the wall 50. In one or more embodiments, some of the heat generated by the energy transfer 24' may be flushed away by the fluid flow 48. The fluid flow 48, in at least one embodiment, may be pulsed periodically, whereby a temperature curve measured by the temperature sensors 20' reflects the periodicity of the fluid flow.

Figure 6:
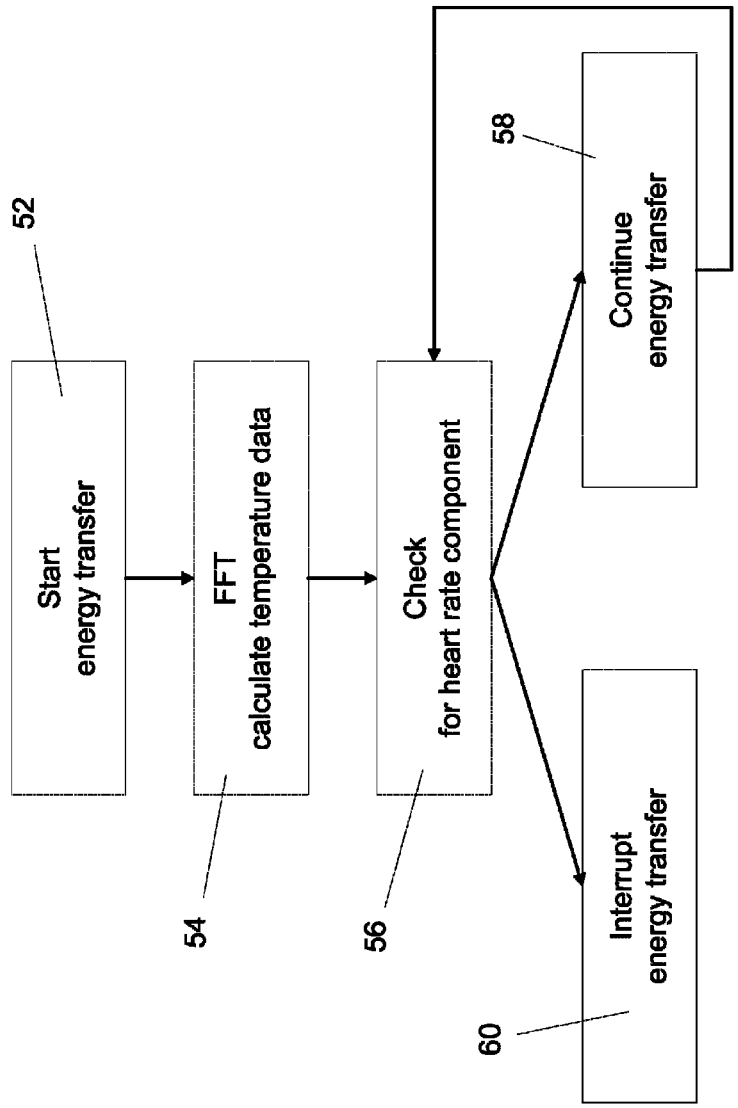
FIG. 6 shows an exemplary flow diagram for a method for evaluating a temperature signal and interruption of an energy transfer.

FIG. 6 shows an exemplary flow diagram, according to one or more embodiments of the invention, for a method including the following steps:

Step 52:

Starting an energy transfer 24, in at least one embodiment, for example from the energy source 30 via a unipolar 14" or bipolar electrode line 14' to a wall 46.

Step 54:

The temperature signal, delivered for example from the temperature sensor 20, may be transformed into the frequency range, in at least one embodiment, using a fast Fourier transform, for example in the evaluation unit 12. In one or more embodiments, other time/frequency transforms, such as a wavelet transform, short-time Fourier transform, or the like, which transform the temperature signal from the time domain into the frequency range may be used. On average, according to one or more embodiments, at least 3.3 measured temperature values per second may be used, such as at least 6.6 measured temperature values per second, or at least 22 measured temperature values per second, in order to carry out the time/frequency transform of the temperature signal. In at least one embodiment, the object of step 54 is to process the temperature signal in such a way that an evaluation of the temperature signal by comparison with predetermined limit values may be achieved in the following step 56, and therefore any other possibility for processing the temperature signal may also be achieved.

Step 56:

In at least one embodiment, the Fourier-transformed temperature signal may be evaluated, for example in the evaluation unit 12, by comparing the temperature amplitudes of a frequency range, for example from 0.2 to 4.2 Hz, or from 0.8 to 3.4 Hz, or from 1.1 to 2.0 Hz with a predetermined limit value of the temperature amplitude. In one or more embodiments, the limit value may include 0.6° C. for the bipolar electrode line 14', wherein a limit value below 0.6° C. indicates constant wall touching of the bipolar electrode line 14'. For the unipolar electrode line 14", the limit value in at least one embodiment may include 0.2° C., wherein a limit value above 0.2° C. indicates constant wall touching of the unipolar electrode line 14". In one or more embodiments, if constant wall touching is provided, step 58 is carried out, and if no constant wall touching is provided, step 60 is instead carried out.

Step 58:

In one or more embodiments, the energy transfer 24 may be continued since constant wall touching, for example of the electrode line 14, has been established, and the method jumps to step 54 in order to analyze further temperature signals. In at least one embodiment, the energy transfer 24 may be continued until the energy source 30 is manually switched off or no wall resistance is determined in step 56, which leads to step 60.

Step 60:

According to one or more embodiments, the energy transfer 24 may be interrupted as soon as no constant wall touching, for example of the electrode line 14, is established. For this purpose, in at least one embodiment, an energy source switch-off signal may be generated for example in the evaluation unit 12 and, during operation, causes the energy transfer 24 for an ablation procedure to be switched off. In one or more embodiments, the energy source switch-off signal may be transmitted, in order to switch off or interrupt the energy source 30, from the evaluation unit 12 to the energy source 30 or to a control unit of the energy source 30, whereupon this switches off or interrupts the energy transfer 24 to the electrode line 14. By way of at least one embodiment, the medical device 10, in which the method shown in FIG. 6 may be used, may be restarted manually. In one or more embodiments, it may be ensured beforehand for example that the electrode line 14 constantly touches a wall by changing its position, since a start-up of the energy transfer 24 after step 52 may otherwise lead to a renewed interruption of the energy transfer 24 due to the absent constant wall touching determined in step 56.

Figure 7:
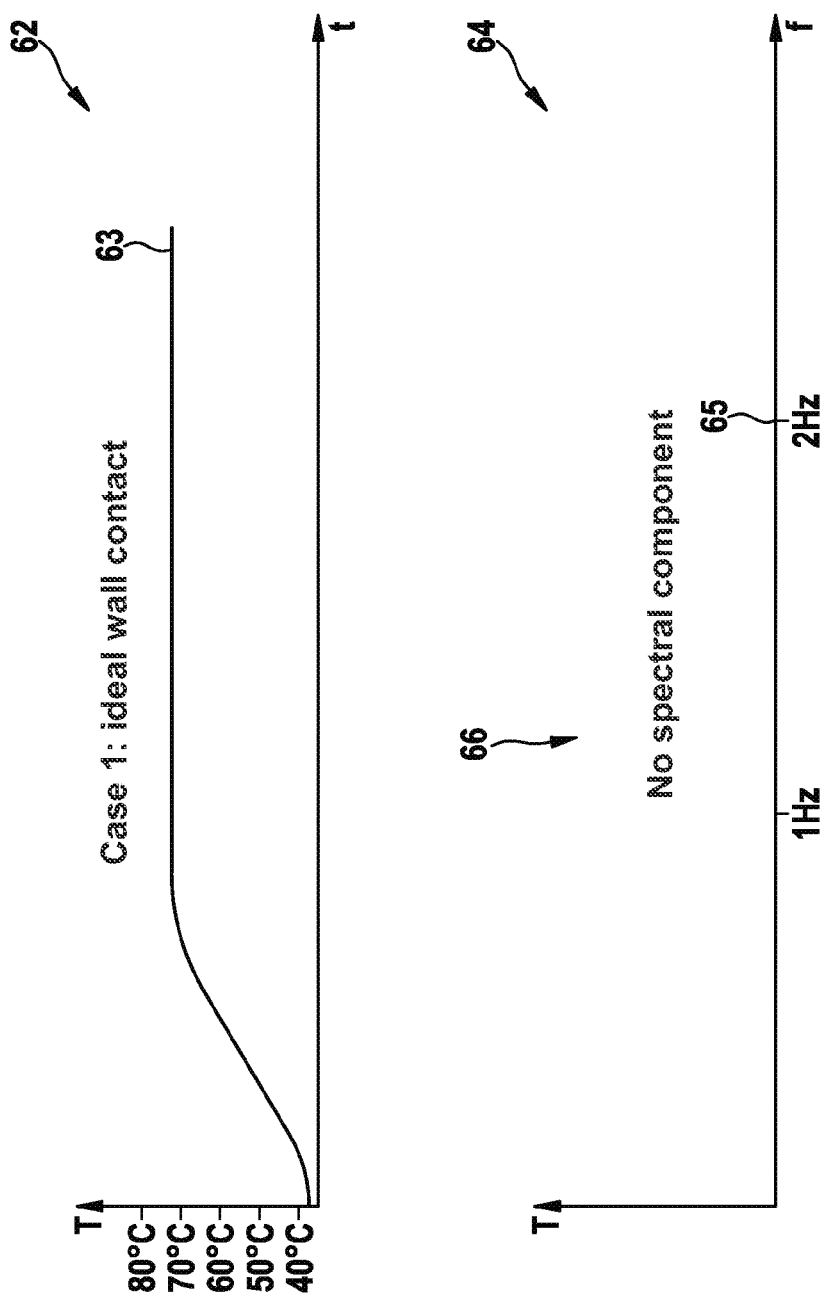
FIG. 7 shows an exemplary temperature signal curve with constant wall touching and a Fourier-transformed temperature signal.

FIG. 7 shows a temperature signal curve 62 with the temperature signal 63 and a temperature signal curve 64, transformed into the frequency range, with a time/frequency-transformed temperature signal 65 for the case of ideal wall contact of a bipolar electrode line 14', according to one or more embodiments of the invention. In at least one embodiment, a frequency range 66 that may be analyzed of the time/frequency-transformed temperature signal 65 around 1 Hz shows no amplitude, and therefore the value may be below the predetermined preferred limit value of 0.6° C. and the evaluation therefore may deliver an evaluation output signal indicating constant wall touching. In at least one embodiment, the frequency range 66 to be analyzed may for example be between 0 Hz (0 bpm (beats per minute)) and 20 Hz (1200 bpm), such as between 0.2 Hz (12 bpm) and 4.2 Hz (252 bpm), or between 0.8 Hz (48 bpm) and 3.4 Hz (204 bpm), or between 1.1 Hz (66 bpm) and 2.0 Hz (120 bpm).

Figure 8:
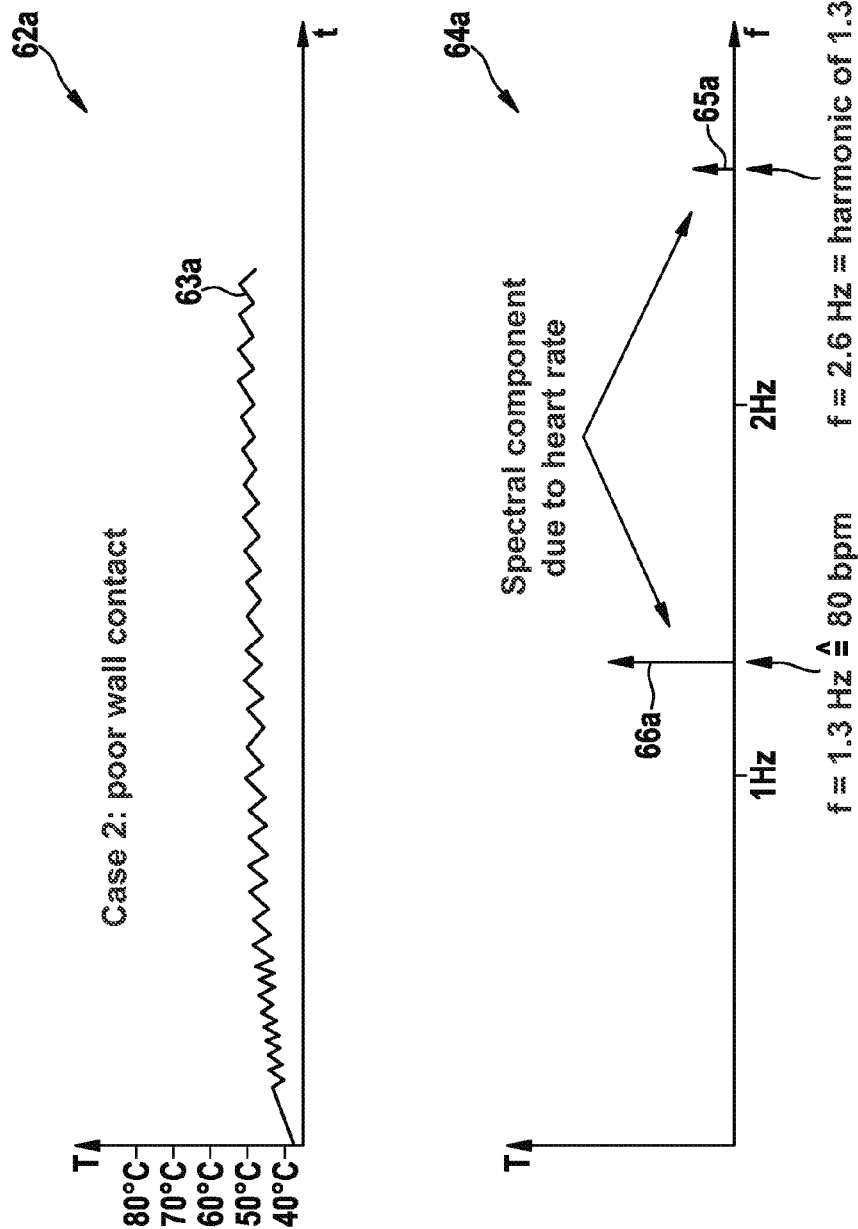
FIG. 8 shows an exemplary temperature signal curve with no constant wall touching and a Fourier-transformed temperature signal.

FIG. 8 shows a temperature signal curve 62a with the temperature signal 63a and a temperature signal curve 64a transformed into the frequency range with the time/frequency-transformed temperature signal 65a for the case of poor wall contact of a bipolar electrode line 14', according to one or more embodiments of the invention. In at least one embodiment, a frequency range 66a may be analyzed around 1 Hz and also a further frequency range around 2 Hz show an amplitude with a value above the predetermined preferred limit value of 0.6° C. In at least one embodiment, the evaluation may therefore deliver an evaluation output signal indicating no constant wall touching of the bipolar electrode line 14'.

Figure 9:
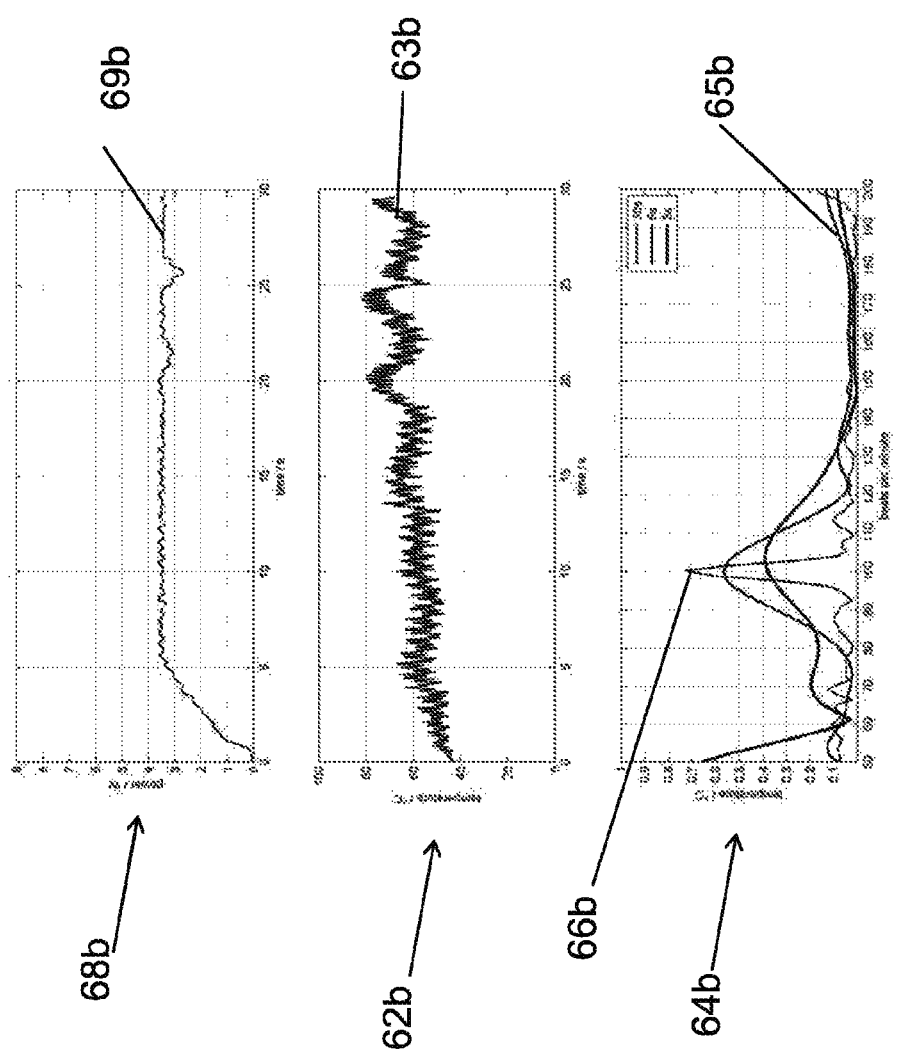
FIG. 9 shows a first example of an energy transfer curve, of a temperature signal curve, and of a Fourier-transformed temperature signal for determining the minimal requirement of the temperature signal for the evaluation of the temperature signal.

FIG. 9 shows the power curve 68b with the power signal 69b, the temperature signal curve 62b with the temperature signal 63b, and a temperature signal curve 64b transformed into the frequency range with the time/frequency-transformed temperature signal 65b, according to one or more embodiments of the invention. In at least one embodiment, the power curve 68b shows a continuous rise of the power signal 69b between t=0 s to t=5 s, which causes a rise of the temperature signal 63b in the temperature signal curve 62b. In one or more embodiments, as the curve continues over time, the power signal 69b may be kept constant. In at least one embodiment, the temperature signal 63b shows periodic fluctuations with different frequencies. In one or more embodiments, the temperature signal curve 64b transformed into the frequency range may be plotted over bpm (beats per minute), as a spectrum, wherein the spectrum of the temperature signal curve may extend from 0.833 Hz (50 bpm) to 3.333 Hz (200 bpm). In at least one embodiment, three different recording periods of the temperature signal 63b, which have been transformed into the frequency range in order to generate a time/frequency-transformed temperature signal 65b, are illustrated in order to establish which recording period is at least necessary to obtain a time/frequency-transformed temperature signal 65b with which constant wall touching of an electrode line 14 may be determined. In one or more embodiments, a peak of the time/frequency-transformed temperature signal 65b may be in the frequency range 66b around 1.667 Hz (100 bpm). In at least one embodiment, the peak may be used to determine constant wall touching. In one or more embodiments, a quality of the constant wall touching or a rough distance between the wall 46 and electrode line 14 may also be estimated via the maximum temperature value of the time/frequency-transformed temperature signal 65b, for example in the preferred frequency range 66b.

According to one or more embodiments, in order to digitalize the analog temperature signal 63b, a number of temperature values per unit of time may be established. In at least one embodiment, a sampling frequency $f_s$ (sampling rate) for digitalizing the temperature data may be at least twice as large as the maximum frequency occurring in the temperature signal 63b. For example, in one or more embodiments, the maximum frequency may be predefined by a pulse rate of a human, for example with values up to 3.333 Hz (200 bpm). In at least one embodiment, the sampling frequency may be at least 6.667 Hz (400 bpm). In one or more embodiments, the sampling frequency $f_s$ may be selected so as to be larger in order to avoid aliasing effects, for example with up to 22 Hz, such as with up to 44 Hz, or with up to 100 Hz. In at least one embodiment, the digitalized temperature data may then be transformed into the frequency range for example with the aid of an algorithm for time/frequency transform, for example fast Fourier transform (FFT) or the like. In one or more embodiments, the smaller the frequency resolution is to be, the greater must be the number N of measured values that are included in the calculation. In at least one embodiment, the number N of measured temperature values follows from the resolution Δf in the frequency range with $$N = \frac{f_s}{\Delta f}.$$

From this, by way of one or more embodiments, the time T for establishing N data values follows with $$T = N \cdot \frac{1}{f_s}.$$

In at least one embodiment, with a sampling frequency of 22 Hz, a recording over 6 s may be necessary for a pulse rate resolution of 10 bpm. According to at least one embodiment, the quickest detection possible of the pulse rate in the temperature data is advantageous. One or more embodiments of the invention may determine within 3 s after onset of an energy transfer whether a component of the pulse rate is present in the data.

Figure 10:
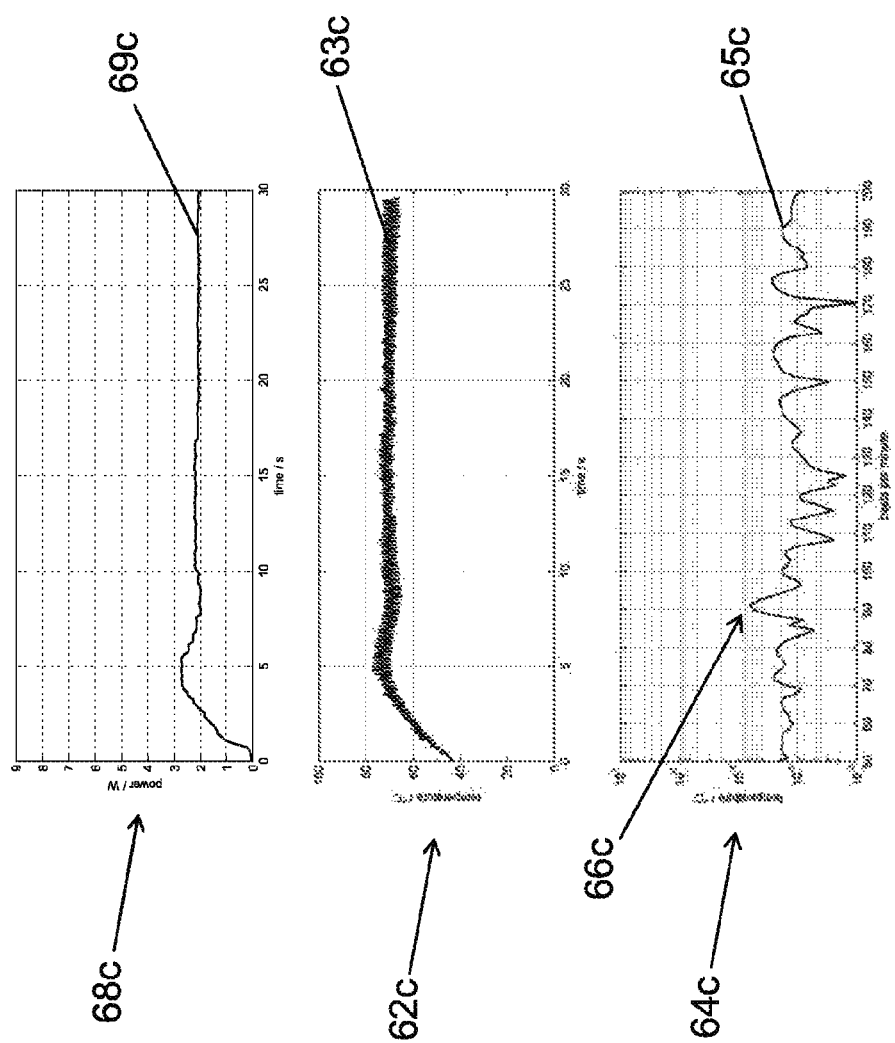
FIG. 10 shows a second example of an energy transfer curve, a temperature signal curve, and a Fourier-transformed temperature signal for constant wall touching of a bipolar electrode line.

FIG. 10 shows exemplary measurements for a bipolar electrode line 14' with constant wall touching according to one or more embodiments of the invention. In at least one embodiment, a temperature signal 63c is shown only for the temperature sensor 20', which displays the higher temperature signal 63c. In one or more embodiments, an average value may be formed from the temperature signals of the temperature sensors 20' or for all temperature signals to be evaluated individually. In contrast to FIG. 9, according to at least one embodiment, the values of the temperature axis of the temperature signal profile 64c transformed into the frequency range are plotted logarithmically. In one or more embodiments, the other measurements or spectra follow the plotting of the measurements or spectra in FIG. 9. In at least one embodiment, the power curve 68c shows a continuous rise of the power signal 69c to approximately t=5 s. Then, in one or more embodiments, the power signal levels off at approximately 2 W. In at least one embodiment of the invention, the temperature signal 63c shows a relatively strong rise of the temperature up to approximately t=5 s correlated with the rise of the energy transfer 24' illustrated in the power signal 69c. In the continued curve over time, according to at least one embodiment, the temperature signal 63c shows a periodic oscillation by approximately 70° C. By way of one or more embodiments, the analysis of the periodic oscillation by transform from the time domain into the frequency range shows, in the temperature spectrum 64c, a relatively flat curve of the time/frequency-transformed temperature signal 65c. In at least one embodiment, the maximum of the time/frequency-transformed temperature signal 65c may be reached in the frequency range 66c at approximately 1.533 Hz (92 bpm). The maximum in this exemplary temperature spectrum 64c, in one or more embodiments, may include a value of approximately 0.065° C. and therefore lies below a predetermined limit value for establishing whether constant wall touching is present. In at least one embodiment, the predetermined limit value may include a value between 0.1° C. and 1.0° C., such as a value between 0.2° C. and 0.8° C., or a value between 0.3° C. and 0.6° C. In one or more embodiments, the temperature spectrum 64c thus shows an evaluation output signal indicating constant wall touching of the electrode line 14'.

By way of at least one embodiment of the invention, further exemplary measurements have shown that reaching a target temperature of 70° C. may lead to a maximum value of 0.08° C. in the temperature spectrum plotted over the frequency if there is constant wall touching of the electrode line 14'.

Figure 11:
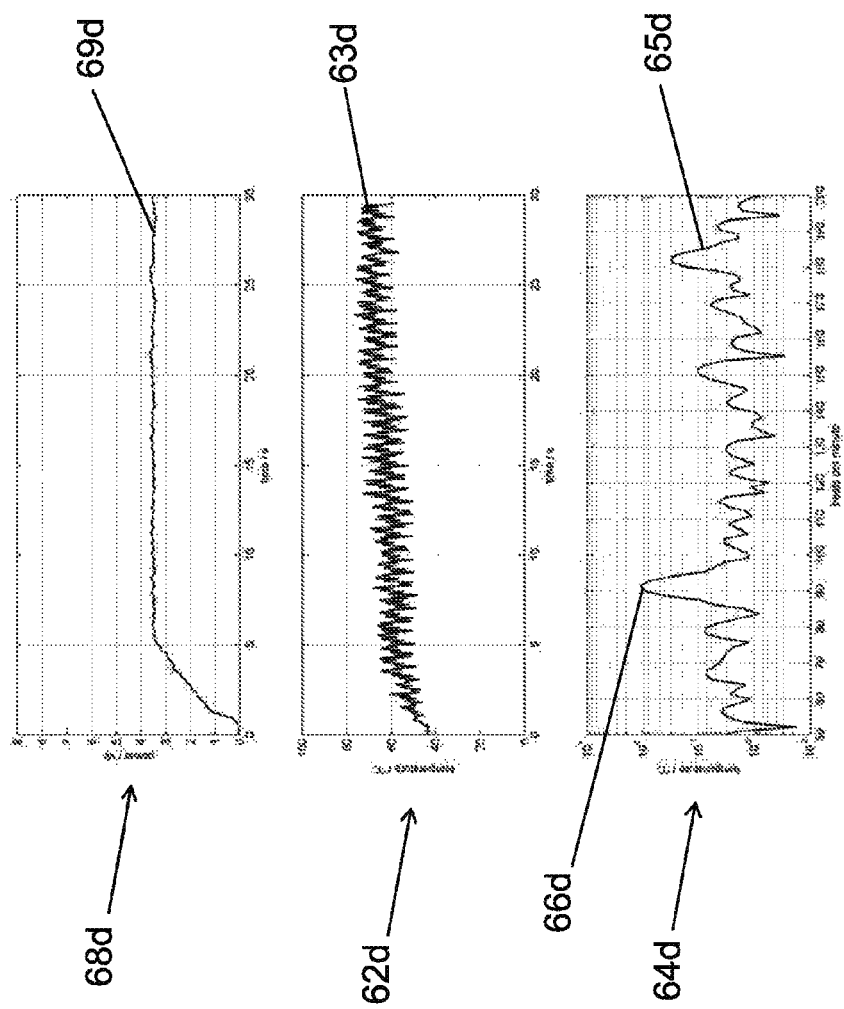
FIG. 11 shows a third example of an energy transfer curve, a temperature signal curve, and a Fourier-transformed temperature signal for no constant wall touching of a bipolar electrode line.

FIG. 11 shows exemplary measurements for a bipolar electrode line 14' with no constant wall touching, according to one or more embodiments of the invention. In contrast to FIG. 10, in at least one embodiment, the curve of the temperature signal 63d in the temperature signal curve 62d shows a greater fluctuation. In one or more embodiments, the power curve 68d shows a slightly higher power signal 69d compared to the power signal 69c in FIG. 10, wherein the ablation electrode pair 22' may include a higher energy transfer 24'. In at least one embodiment, the temperature spectrum 64d plotted over the frequency shows a more strongly fluctuating curve of the time/frequency-transformed temperature signal 65d compared to the time/frequency-transformed temperature signal 65c. In at least one embodiment, in the frequency range 66d to be analyzed, a peak is formed, which, with a value of approximately 1.0° C., lies above the predetermined limit value. As such, in one or more embodiments, the temperature spectrum 64d shows an evaluation output signal indicating no constant wall touching of the electrode line 14'.

According to one or more embodiments, further exemplary measurements have shown that the failure to reach a target temperature of 70° C. may lead to a maximum value of 0.6° C. to 1.0° C. in the temperature spectrum plotted over the frequency if no constant wall touching of the electrode line 14' is present.

In one or more embodiments, a summary of the results from FIG. 10 and FIG. 11 leads to the finding that good wall contact or constant wall touching may be present with a limit value below 0.6° C. In at least one embodiment, constant wall touching of a bipolar electrode line 14' may be identified on the basis of the fact that no increased temperature value of a frequency range corresponding to the periodic fluid flow may be identified. The fluid flow, in one or more embodiments, for example a blood flow in a renal artery, may be identified in the temperature signal according to the distance between the wall and electrode line or ablation electrode pair, since the heat that is produced during the energy transfer is flushed away by the fluid flow and therefore periodically lowers the level of the temperature signal. With greater distance from the wall, in at least one embodiment, with no constant wall touching, the temperature fluctuation may be higher, since more heat is transferred to the fluid. In one or more embodiments, the fluid flow may also have a variance in the periodicity, for example with a continuously changing heart rhythm. As such, in at least one embodiment, the variance may lead to a widening of the frequency range preferably to be analyzed.

By way of one or more embodiments, the establishment of the constant wall touching may be used for example to switch off an ablation generator or an energy source if ablation electrodes connected thereto are not in contact with a wall (not shown).

Figure 12:
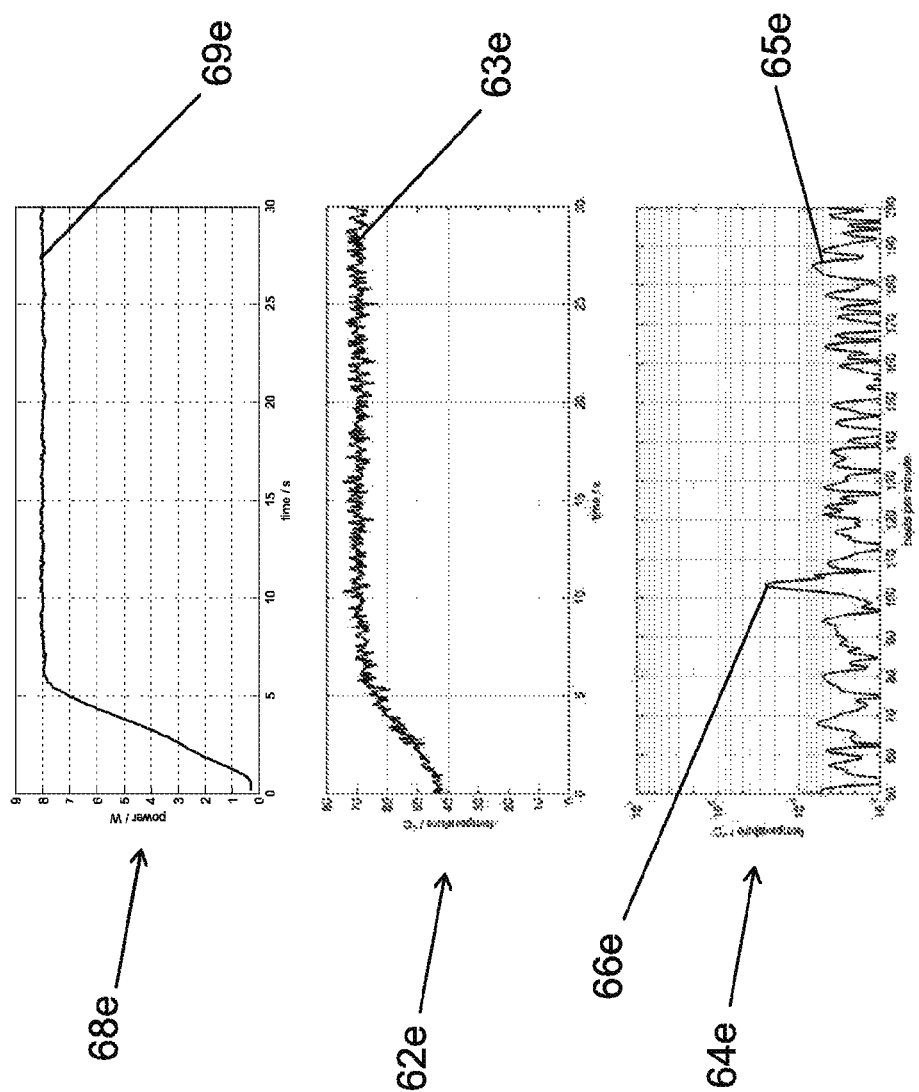
FIG. 12 shows a fourth example of an energy transfer curve, a temperature signal curve, and a Fourier-transformed temperature signal for constant wall touching of a unipolar electrode line.

FIG. 12 shows exemplary measurements for a unipolar electrode line 14'' with constant wall touching according to one or more embodiments of the invention. In at least one embodiment, the temperature signal 63e is shown in the temperature signal curve 62e for the temperature sensor 20". In one or more embodiments, the power curve 68e shows a continuous rise of the power signal 69e to approximately t=6 s. As the curve continues over time, in at least one embodiment, the energy transfer 24" is kept constant. In one or more embodiments, the temperature signal 63e follows the rise of the power signal 69e to t=6 s and then oscillates around a value of approximately 70° C. According to at least one embodiment, the time/frequency transform of the temperature signal 63e into the frequency range may deliver a temperature spectrum 64e, of which the time/frequency-transformed temperature signal 65e in a frequency range 66e shows a peak of approximately 0.26° C.

In one or more embodiments, with the use of a unipolar electrode line 14", a neutral electrode or adhesive electrode may be additionally secured outside the fluid flow system, for example to the body. In at least one embodiment, the area of such a neutral electrode may be a number of times greater than the area of the ablation electrode 22". In contrast to the bipolar electrode line 14', in one or more embodiments, a periodic oscillation may be clearly identified in the time/frequency-transformed temperature signal 65e. In this case, in at least one embodiment, this indicates however constant wall touching of the unipolar electrode line 14", which is supported by the level of the temperature signal. In one or more embodiments, the temperature spectrum 64e thus shows an evaluation output signal indicating constant wall touching of the unipolar electrode line 14".

Figure 13:
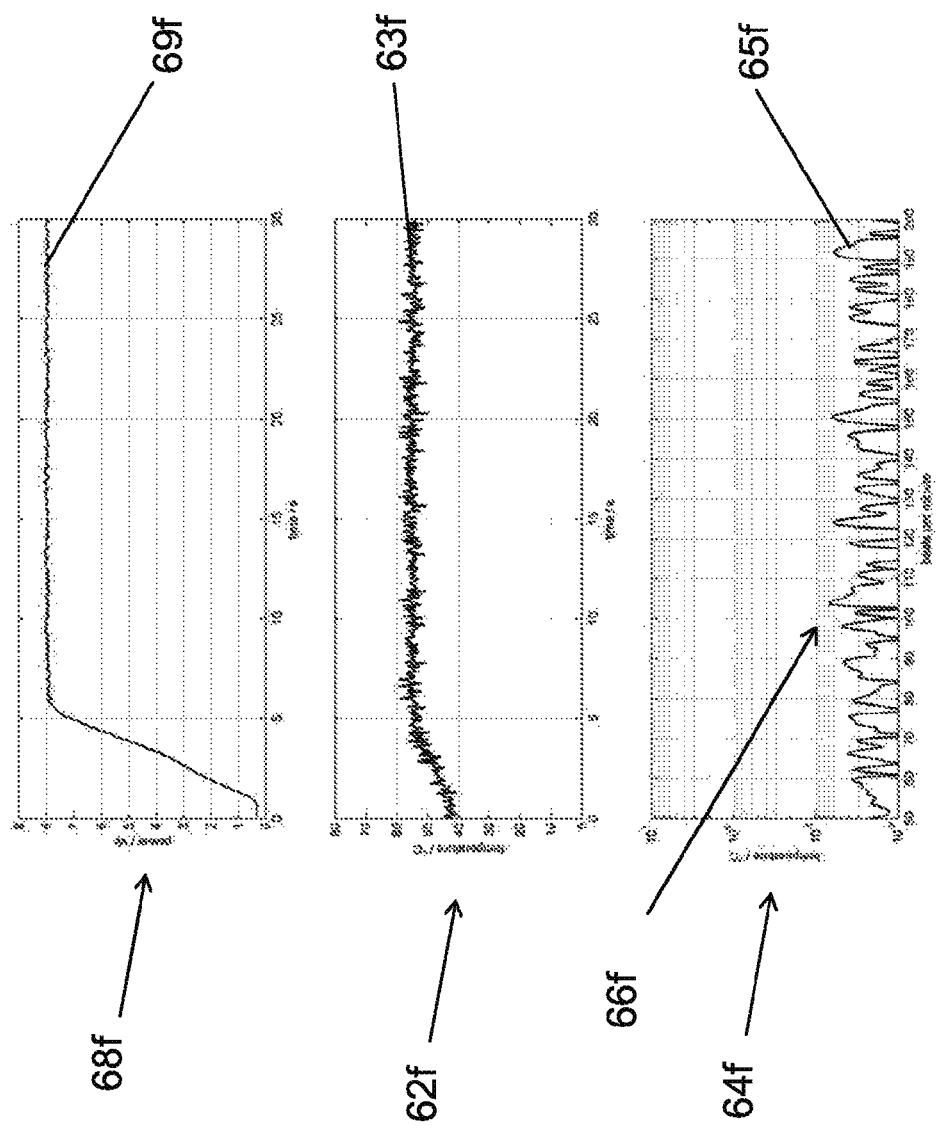
FIG. 13 shows a fifth example of an energy transfer curve, a temperature signal curve, and a Fourier-transformed temperature signal for no constant wall touching of a unipolar electrode line.

FIG. 13 shows exemplary measurements for a unipolar electrode line 14" with no constant wall touching according to one or more embodiments of the invention. In at least one embodiment, the curve of the power signal 69f in the power curve 68f may be largely identical to the power signal 69e from FIG. 12. In one or more embodiments, the curve of the temperature signal 63f in the temperature signal curve 62f may be flatter however and may only reach a maximum height of approximately 60° C. In at least one embodiment, the temperature signal 63f may oscillate around a value of approximately 55° C. According to one or more embodiments, the time/frequency transform may not deliver in the temperature spectrum 64f any sever fluctuations of the time/frequency-transformed temperature signal 65f, which also may not have a significant peak in the preferred frequency range 66f. In conjunction with the lower temperature of approximately 55° C., by way of one or more embodiments, it may be concluded that in this case there is a poorer wall contact, or that the unipolar electrode line 14" may have a greater wall distance 50 from the wall 46 compared to FIG. 12. In at least one embodiment, the temperature spectrum 64f thus shows an evaluation output signal indicating no constant wall touching of the unipolar electrode line 14".

By way of one or more embodiments, exemplary measurements have shown that the failure to reach a target temperature of 70° C. may lead to a maximum value of 0.1° C. in the temperature spectrum according to frequency if there is no constant wall touching of the electrode line 14", whereas constant wall touching may be found for maximum values above 0.2° C.

In at least one embodiment, to measure a wall contact before a relatively long energy transfer 24, a lower amount of energy may be transferred. According to one or more embodiments, this may be carried out only for a few seconds, for example 6 s, preferably 3 s, in order to determine constant wall touching or, where necessary, to adjust the position of the electrode line 14.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10 medical device
12 evaluation unit
14 electrode line
16 renal artery
18 kidney
20 temperature sensor
22 ablation electrode
24 energy transfer
26 flexible tube
28 aorta
30 energy source
32 sympathetic nerve fibers
33 distal end of the electrode line
34 electrical line
36 sensor line
38 temperature signal amplifier
40 analog-to-digital converter
42 microcontroller unit
44 computer unit
46 wall
48 fluid flow
50 wall distance
62 temperature signal curve according to time
63 temperature signal
64 temperature signal curve transformed into the frequency range (temperature spectrum)
65 time/frequency-transformed temperature signal
66 preferred frequency range for establishment of constant wall touching
68 power curve according to time
69 power signal

What is claimed is:
1. A medical device comprising:
an evaluation unit, and
an electrode line,
    wherein said electrode line comprises at least one temperature sensor that delivers a temperature signal to the evaluation unit,
    wherein the evaluation unit
        evaluates periodic fluctuations of a signal level of the temperature signal, and
        generates an evaluation output signal qualifying constant wall touching of the electrode line based on whether periodic fluctuations of a signal level of the temperature signal lie below or above a predetermined limit value, and
    wherein the electrode line is a unipolar ablation electrode line comprising an ablation electrode that delivers unipolar ablation, and wherein the evaluation unit one or more of
        generates an evaluation output signal indicating constant wall touching of the electrode line if periodic fluctuations of a signal level of the temperature signal lie above the predetermined limit value, and generates an evaluation output signal indicating no constant wall touching of the electrode line if periodic fluctuations of a signal level of the temperature signal lie below the predetermined limit value.

2. The medical device as claimed in claim 1, wherein the predetermined limit value comprises a value between 0.05° C. and 0.6° C., a value 0.1° C. and 0.4° C., or a value between 0.2° C. and 0.3° C.

3. The medical device as claimed in claim 1, wherein the evaluation unit evaluates the periodic fluctuations of a signal level of the temperature signal using a time/frequency transform outputting a time/frequency-transformed temperature signal.

4. The medical device as claimed in claim 3, wherein the evaluation unit evaluates a frequency range of the time/frequency-transformed temperature signal between 0.2 Hz and 4.2 Hz, between 0.8 Hz and 3.4 Hz, or between 1.1 Hz and 2.0 Hz.

5. The medical device as claimed in claim 1, wherein the electrode line is flexible.

6. A method for evaluating a temperature signal using a medical device comprising an evaluation unit, and an electrode line which comprises at least one temperature sensor, wherein the method comprises:
providing a temperature signal via the at least one temperature sensor, wherein the at least one temperature sensor delivers the temperature signal to the evaluation unit, and
evaluating periodic fluctuations of a signal level of the temperature signal via the evaluation unit, wherein an evaluation output signal qualifying constant wall touching of the electrode line is generated via the evaluation unit based on whether periodic fluctuations of a signal level of the temperature signal lie below or above a predetermined limit value,
wherein the evaluation of the periodic fluctuations of a signal level of the temperature signal is carried out in the evaluation unit using a time/frequency transform of the temperature signal.

7. The method as claimed in claim 6, wherein at least 6.6 measured temperature values per second are evaluated from the temperature signal.

8. The method as claimed in claim 6, wherein the medical device further comprises an energy source, and wherein the method further comprises starting an energy transfer of the energy source to the electrode line prior to said providing a temperature signal.

9. The method as claimed in claim 8, wherein the method further comprises terminating the energy transfer to the electrode line if the evaluation unit generates an evaluation output signal indicating no constant wall touching of the electrode line.

10. A medical device comprising:
an evaluation unit, and
an electrode line,
wherein said electrode line comprises at least one temperature sensor that delivers a temperature signal to the evaluation unit,
wherein the evaluation unit
evaluates periodic fluctuations of a signal level of the temperature signal, and
generates an evaluation output signal qualifying constant wall touching of the electrode line based on whether periodic fluctuations of a signal level of the temperature signal lie below or above a predetermined limit value, and,
wherein the evaluation unit evaluates the periodic fluctuations of a signal level of the temperature signal using a time/frequency transform outputting a time/frequency-transformed temperature signal.

11. The medical device as claimed in claim 10, wherein the evaluation unit evaluates a frequency range of the time/frequency-transformed temperature signal between 0.2 Hz and 4.2 Hz, between 0.8 Hz and 3.4 Hz, or between 1.1 Hz and 2.0 Hz.

12. The medical device as claimed in claim 10, wherein the electrode line is a bipolar ablation electrode line comprising an ablation electrode pair that delivers bipolar ablation, and wherein the evaluation unit one or more of
generates an evaluation output signal indicating constant wall touching of the electrode line if periodic fluctuations of a signal level of the temperature signal lie below the predetermined limit value, and
generates an evaluation output signal indicating no constant wall touching of the electrode line if periodic fluctuations of a signal level of the temperature signal lie above the predetermined limit value.

13. The medical device as claimed in claim 12, wherein the predetermined limit value comprises a value between 0.1° C. and 1.0° C., a value between 0.2° C. and 0.8° C., or a value between 0.3° C. and 0.6° C.

14. The medical device as claimed in claim 12, wherein the at least one temperature sensor is arranged in a vicinity of the at least one ablation electrode.

15. The medical device as claimed in claim 12, further comprising an energy source electrically connected to the electrode line and the evaluation unit,
wherein the energy source outputs energy to the electrode line, and
wherein the evaluation unit generates an energy source switch-off signal to switch off the energy source if the evaluation unit generates an evaluation output signal indicating no constant wall touching of the electrode line, wherein energy transfer of the ablation process is switched off during operation.

16. A method for evaluating a temperature signal using a medical device comprising an evaluation unit, and an electrode line which comprises at least one temperature sensor, wherein the method comprises:
providing a temperature signal via the at least one temperature sensor, wherein the at least one temperature sensor delivers the temperature signal to the evaluation unit, and
evaluating periodic fluctuations of a signal level of the temperature signal via the evaluation unit, wherein an evaluation output signal qualifying constant wall touching of the electrode line is generated via the evaluation unit based on whether periodic fluctuations of a signal level of the temperature signal lie below or above a predetermined limit value,
wherein at least 6.6 measured temperature values per second are evaluated from the temperature signal.

* * * * *